United States Patent [19]

Nakhgevany

[11] Patent Number: 4,892,095
[45] Date of Patent: Jan. 9, 1990

[54] ENDOTRACHEAL TUBE

[76] Inventor: Karim B. Nakhgevany, 302 Fairview Rd., Narberth, Pa. 19072

[21] Appl. No.: 27,287

[22] Filed: Mar. 17, 1987

[51] Int. Cl.$^4$ .............................................. A61M 16/00
[52] U.S. Cl. ............................ 128/207.14; 128/200.26
[58] Field of Search ....................... 128/207.14, 207.15, 128/200.26, 748, 780

[56] References Cited

U.S. PATENT DOCUMENTS

| Re. 32,306 | 12/1986 | Waters | 604/165 |
|---|---|---|---|
| 2,862,498 | 12/1958 | Weekes | 128/207.4 |
| 3,683,908 | 8/1972 | Michael et al. | 128/207.15 |
| 3,754,554 | 8/1973 | Felbarg | 128/351 |
| 3,905,361 | 9/1975 | Hewson et al. | 128/145.5 |
| 3,948,273 | 4/1976 | Sanders | 128/351 |
| 4,026,296 | 5/1977 | Stoy et al. | 128/349 B |
| 4,041,936 | 8/1977 | Carden | 128/6 |
| 4,244,362 | 1/1981 | Anderson | 128/207.15 |
| 4,246,897 | 1/1981 | Muto | 128/207.15 |
| 4,278,081 | 7/1981 | Jones | 128/207.15 |
| 4,327,720 | 5/1982 | Bronson et al. | 128/207.15 |
| 4,431,005 | 2/1984 | McCormick | 128/207.14 |
| 4,468,216 | 8/1984 | Muto | 604/43 |
| 4,497,318 | 2/1985 | Donmichael | 128/207.15 |
| 4,691,701 | 9/1987 | Williams | 128/207.14 |

Primary Examiner—David A. Wiecking
Assistant Examiner—Aaron J. Lewis
Attorney, Agent, or Firm—Seidel, Gonda, Lavorgna & Monaco

[57] ABSTRACT

An endotracheal intubation device includes an inner flexible guide tube and an outer tube. The guide tube has a blunt end, an opened end, and an opening adjacent the blunt end which is adapted for passing a gas therethrough. The outer tube has open ends and is adapted for sliding and telescoping passage over the guide tube. An inflatable cuff, which is adapted for engagement with the trachea, is adjacent a distal end of the outer tube. The guide tube is inserted into a passageway of the patient. After determining that the guide tube is in the trachea, the outer tube is slid over the guide tube. Then, the guide tube is removed from the outer tube.

4 Claims, 2 Drawing Sheets

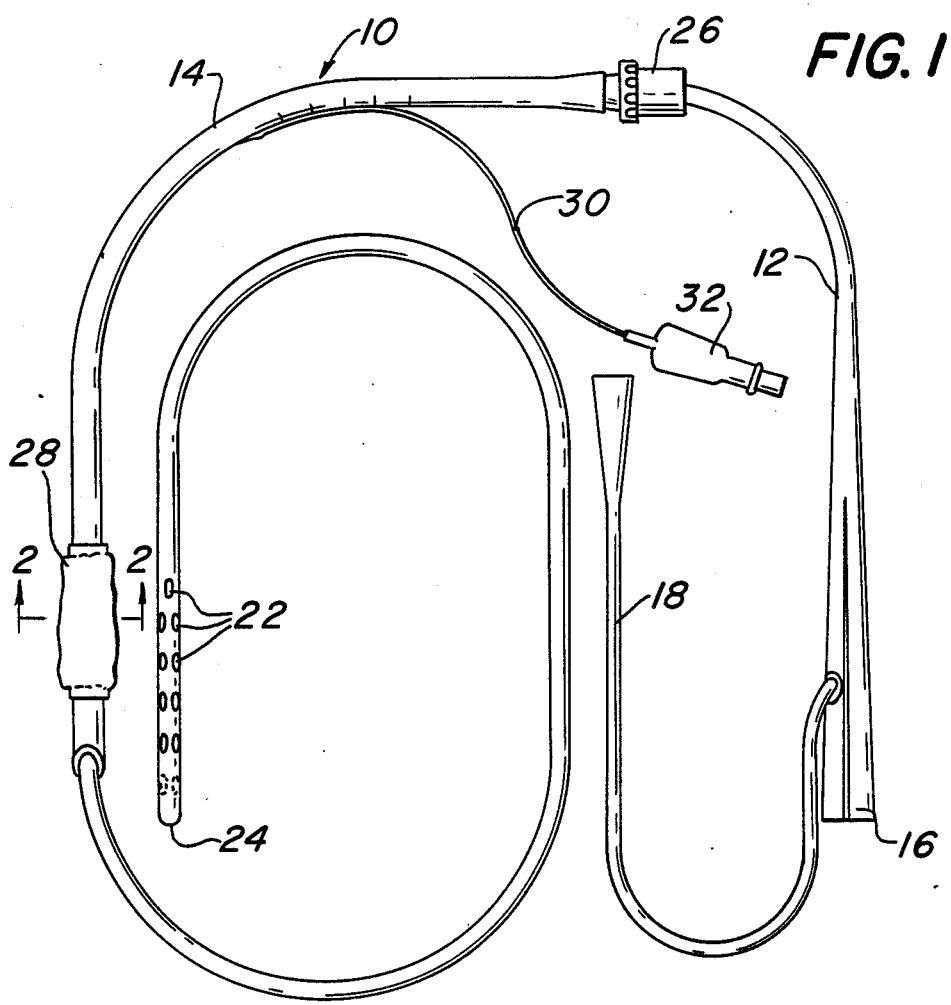
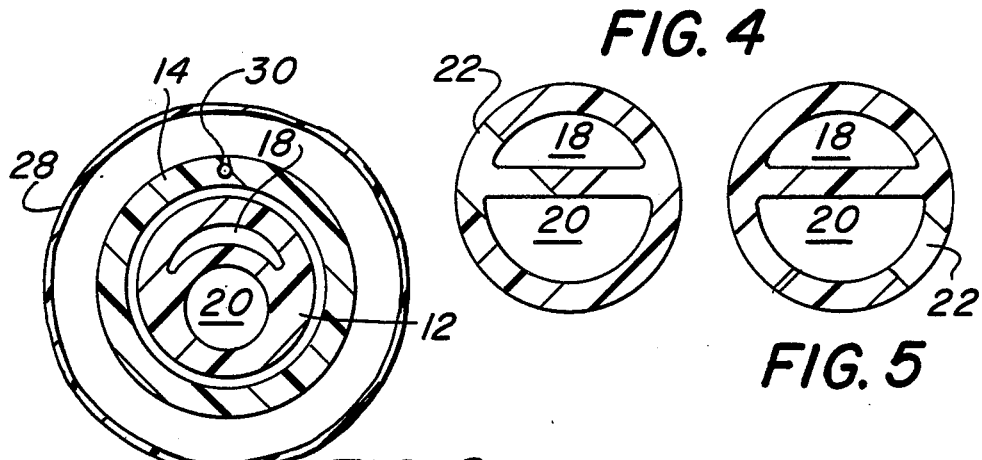

ENDOTRACHEAL TUBE

SCOPE OF THE INVENTION

This invention is directed to an endotracheal tube device and a method of using the same.

BACKGROUND OF THE INVENTION

Emergency endotracheal intubation and especially emergency endotracheal intubation in the trauma setting with possible cervical spine injury have a significantly high complication rate. Not only are these patients frequently unstable and thus making the need for rapid intubation crucial; but the conditions in the field and the experience of the persons performing the intubation are certainly less optimal than in the operating room setting.

Complications of endotracheal intubation are numerous and frequent In one study, 38 complications occurred in 24 of 43 patients requiring emergency room endotracheal intubation. Complications include aspiration, interruption of CPR (cardiopulmonary resuscitation), prolonged period required for intubation, right mainstem bronchus intubation, tube damage during insertion, and pneumothorax (an accumulation of air or gas in the pleural space). In another study, nearly one-third of all endotracheal intubations took over two minutes, and one fifth required four or more attempts. For standard orotracheal intubation with the neck extended, a curved or flat larynogoscope is used to visualize the vocal cords during tube insertion. Thus, the present situation of orotracheal or nasotracheal intubation has room for improvement.

The esophageal gastric tube airway is infrequently used now, but in the past was used regularly by emergency room technicians. This device is inserted blindly into the esophagus The advantage is the ease of insertion and that no special training is required The disadvantage is that the ventilation is much less efficient than with the endotracheal tube. In one study, the esophegeal gastric airway provided blood gas on an average pH of 7.12, p02 of 77, pC02 of 78, while the endotracheal tube produced pH of 7.34, p02 of 265 and pC02 of 35.

Other techniques include the optical stylet and fiberoptic bronchoscope. These methods use either the rigid stylet or the flexible bronchoscope to visualize the vocal cords, and the endotracheal tube is inserted under direct visual guidance.

Invasive techniques include percutaneous jet ventilation, cricothyroidotomy, and emergency tracheostomy. Jet ventilation requires insertion of a catheter into the trachea through the cricothroid membrane, and with rapid ventilation, can provide excellent respiratory support but for only limited periods of time, about one hour. Cricothyroidotomy may be performed with relative ease and rapidity by inserting a blade into the neck through the cricothroid membrane. This method is easily learned but has increased risk of tracheal stenosos over the standard tracheostomy. Although cricotyroidotomy is hardly a method for routine use to provide an airway in the trauma patient, it is very useful in selected patients. Emergency tracheostomy is certainly an excellent means of obtaining ventilatory support for a patient, but has many risks in the emergency setting, can be very difficult and requires a great deal of training. Therefore, it is not suitable for emergency endotracheal intubation. Finally retrograde endotracheal intubation over a guide wire is performed by piercing the cricothroid membrane with a needle, then advancing a flexible wire up through the trachea and vocal cords and out the mouth, and then placing the endotracheal tube over the wire and guiding it into the trachea. This method is very useful for difficult endotracheal intubations, but requires special training, special equipment and an invasive technique. Therefore, there are many alternatives to standard orotracheal intubation which can be used in emergency intubations or especially in emergency intubations in the trauma setting, but each requires specialized training and/or equipment not routinely available to emergency workers. Additionally, many of these methods require manipulation of the neck which may be contradicted in trauma patients, and each technique has a long list of complications.

SUMMARY OF THE INVENTION

A method of endotracheal intubation is disclosed. The steps of the method include:

inserting a first tube into a passageway of a patient;

auscultating over a stomach of a patient to determine that the first tube is not present in the stomach;

sliding a second tube over the first tube whereby a distal end of the second tube is positioned within a trachea of the patient; and removing the first tube from the second tube.

An endotracheal intubation device includes an inner flexible guide tube and an outer tube. The guide tube has a blunt end, an opened end, and an opening adjacent the blunt end which is adapted for passing a gas therethrough. The outer tube has open ends and is adapted for sliding and telescoping passage over the guide tube. An inflatable cuff, which is adapted for engagement with the trachea, is adjacent a distal end of the outer tube. The guide tube is inserted into a passageway of the patient. After determining that the guide tube is in the trachea, the outer tube is slid over the guide tube. Then, the guide tube is removed from the outer tube.

This device will make endotracheal intubation an easy and safe technique that can be done by less trained individuals in the hospital emergency room as well as in the field.

DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 1 is an illustration of the preferred embodiment of the present invention.

FIG. 2 is a sectional view of the preferred embodiment taken along the lines 2—2 of FIG. 1.

FIG. 4 is a sectional view of the preferred embodiment taken along the lines 4—4 of FIG. 3.

FIG. 5 is a sectional view of the preferred embodiment taken along the lines 5—5 of FIG. 3.

DETAILED DESCRIPTION OF THE INVENTION

Figure 3:
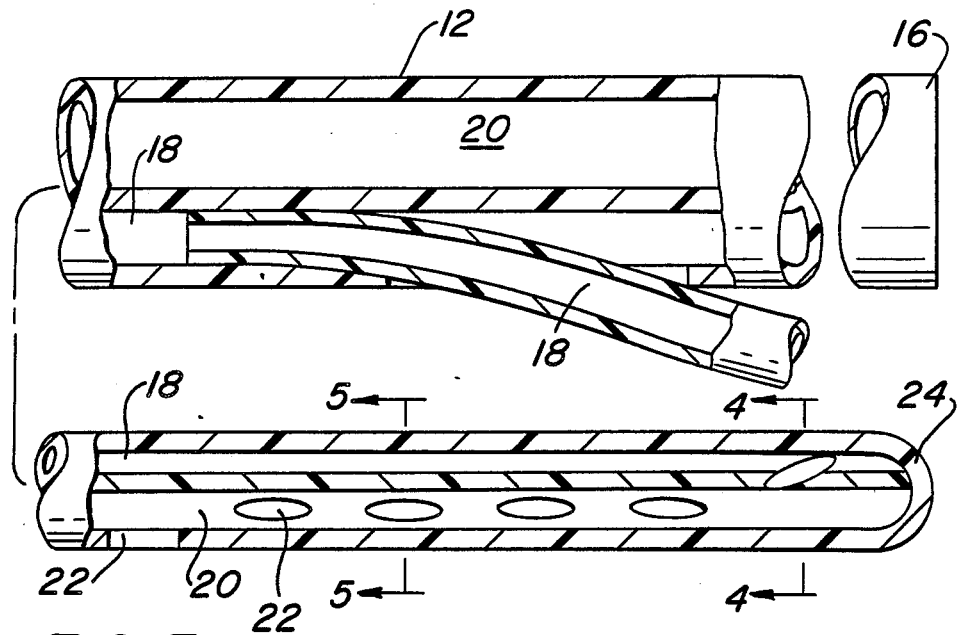
FIG. 3 is an enlarged view of the preferred embodiment, parts broken away for clairity.

Referring to the drawings wherein like numerals indicate like elements there is shown in FIG. 1 an illustration of the preferred embodiment of the present invention generally designated 10.

The endotracheal tube system 10 generally comprises an inner guide tube 12 and an outer tube 14. All components of system 10 are preferably made of plastics, well known to those of ordinary skill in the art. The guide tube 12 has a length greater than that of outer tube 14. Outer tube 14 is adapted for sliding and telescoping passage over guide tube 12. Accordingly, the outer diameter of guide tube 12 is less than the inner diameter of outer tube 14.

Preferably, guide tube 12 is approximately 48 inches long and is made of an 18 French flexible tube. It is important that the tube be sufficiently flexible so as not to injure the larynx, trachea or esophagus of the patient while the guide tube is inserted into the patient. The guide tube 12 includes a blunt end 24 and a widened opened end 16. Widened opened end 16 is adapted for receipt of a standard catheter syringe. The blunt end 24 is closed. A plurality of openings 22 are located adjacent the blunt end 24. Preferably, an oxygen passageway 18 is integral with guide tube 12. Oxygen passageway 18 is provided for supplying oxygen to the patient. FIGS. 2-5 illustrate various sectional views of the internal construction of guide tube 12. The oxygen passageway may have an internal diameter of approximately 1 mm (of course this dimension can be varied).

The outer tube 14 preferably has an internal diameter of approximately 8-10 mm. (of course this dimension can be varied Specifically smaller patient, i.e. children, may not use the same size device as large patients, i.e. adults.) Adjacent a distal end of the outer tube 14 is an inflatable cuff 28. Inflatable cuff 28 is adapted for inflatable engagement with trachea 34. (See FIG. 6.) At the proximal end of outer tube 14 is a collar 26. Collar 26 is optional. An inflation passageway 30 is in communication with cuff 28. (See FIGS. 1 and 2.) At the terminal end of the inflation passageway 30 is a valve 32. Valve 32 is well-known to those of ordinary skill in the art.

Figure 6:
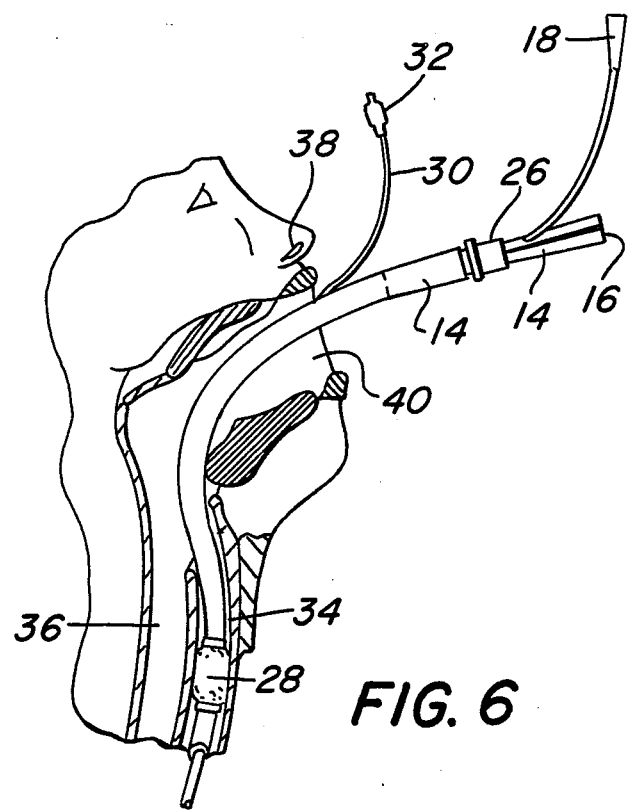
FIG. 6 is an illustration of the preferred embodiment in use and prior to the removal of the guide tube.

Referring to FIG. 6, the method by which the endotracheal tube system 10 is used will be described. Please note that the method will be described with the system 10 passing through the oral cavity 40 of the patient. However, the system 10 may be passed through the nasal passage 38 of the patient.

The inner guide tube 12 is inserted through the oral passage 40 of the patient. The guide tube 12 will either enter the esophagus 36 or the trachea 34. Once guide tube 12 is inserted, gas is blown through tube 12 and the stomach is auscultated. If the guide tube is in the stomach, then the listener will hear a "gurgling sound". If the guide tube has entered the trachea, the listener will hear no sound.

After the guide tube 12 is inserted into the trachea, the outer tube 14 is passed over the guide tube 12. The cuff 28 is inflated and bears against the walls of the trachea 34. The guide tube 12 is then removed from the outer tube.

The specific dimensions recited above are merely explemary and are not meant to limit the invention. Furthermore, the device disclosed herein is not limited solely to use in trauma situations, but may be used whenever intubation is required.

The present invention may be embodied in other specific forms without departing from the spirit or essential attributes thereof and, accordingly, reference should be made to the appended claims, rather than to the foregoing specification, as indicating the scope of the invention.

I claim:

1. A method for endotracheal intubation comprising the steps of:
    (a) providing a flexible guide tube having a length sufficiently long to extend between a patient's face and stomach and having a closed blunt end with at least one opening adjacent said closed end, said guide tube being adapted for passing a gas therethrough to said opening;
    (b) inserting said guide tube through a facial passageway of the patient;
    (c) blowing gas into said guide tube;
    (d) auscultating over said patient's stomach;
    (e) determining the location of said guide tube by listening for a gurgle-like sound, if said gurgle-like sound is made then said guide tube is removed and reinserted, if said gurgle like sound is not heard then said guide tube is properly located within said patient's trachea;
    (f) sliding an endotracheal tube over said guide tube while a portion of said guide tube is positioned in said patient's trachea; and
    (g) removing said guide tube from said patient.

2. The method according to claim 1 further comprising the step of:
    inserting said guide tube through said patient's mouth.

3. The method according to claim 1 further comprising the step of:
    inserting said guide tube through said patient's nose.

4. The method according to claim 1 further comprising the step of:
    providing said endotracheal tube with an inflatable cuff which when inflated engages said patient's trachea.

* * * * *